United States Patent [19]

(12) United States Patent
Fornasier et al.

(10) Patent No.: US 10,571,451 B2
(45) Date of Patent: Feb. 25, 2020

(54) METHOD AND SYSTEM FOR MONITORING THE DRILLING OF A WELLBORE

(71) Applicant: Geoservices Equipements, Roissy en France (FR)

(72) Inventors: Ivan Fornasier, Roissy-en-France (FR); Ilaria De Santo, Sugar Land, TX (US); David Cook, Sugar Land, TX (US); Jacques Chedotal, Pau (FR); Slim Hbaieb, Roissy-en-France (FR)

(73) Assignee: GEOSERVICES EQUIPEMENTS, Roissy en France (FR)

( * ) Notice: Subject to any disclaimer, the term of this patent is extended or adjusted under 35 U.S.C. 154(b) by 385 days.

(21) Appl. No.: 15/423,616

(22) Filed: Feb. 3, 2017

(65) Prior Publication Data

US 2017/0226852 A1     Aug. 10, 2017

(30) Foreign Application Priority Data

Feb. 4, 2016    (EP) .................................... 16290024

(51) Int. Cl.
*G01N 33/28*     (2006.01)
*E21B 21/01*     (2006.01)

(52) U.S. Cl.
CPC ......... *G01N 33/2823* (2013.01); *E21B 21/01* (2013.01)

(58) Field of Classification Search
CPC .... G01N 33/2823; E21B 21/01; E21B 49/086
See application file for complete search history.

(56) References Cited

U.S. PATENT DOCUMENTS

| 7,823,656 | B1* | 11/2010 | Williams ................ E21B 21/01 175/206 |
| 2006/0202122 | A1* | 9/2006 | Gunn ...................... E21B 21/01 250/339.13 |
| 2011/0303463 | A1* | 12/2011 | Lessi ..................... E21B 21/067 175/50 |
| 2015/0000751 | A1* | 1/2015 | Nicholson ................. F16K 1/22 137/2 |
| 2015/0260703 | A1* | 9/2015 | Mitchell ................. E21B 47/00 73/19.09 |
| 2016/0115786 | A1* | 4/2016 | Breviere ............... E21B 49/005 73/152.23 |
| 2016/0160641 | A1* | 6/2016 | Rowe ..................... E21B 21/01 250/282 |

FOREIGN PATENT DOCUMENTS

| EP | 1710575 A2 | 10/2006 |
| EP | 1887343 A1 | 2/2008 |
| EP | 2380017 A2 | 10/2011 |

\* cited by examiner

*Primary Examiner* — Manuel L Barbee

(57) ABSTRACT

A method of monitoring the drilling of a wellbore having a drilling fluid that circulates in the wellbore during drilling, comprises:

Extracting a plurality of gaseous compounds from a sample of drilling fluid exiting the wellbore, Measuring a quantity $y(i)$ of at least a group of compounds, each group comprises comprising at least one extracted gaseous compound, Determining, from the measured quantity $y(i)$ and an extraction coefficient $\rho(i)$ associated to each group, the content $x(i)$ of each group of gaseous compounds present in the sample of drilling fluid, Deriving a drilling indicator from the content $x(i)$ of at least one group of gaseous compounds.

19 Claims, 2 Drawing Sheets

METHOD AND SYSTEM FOR MONITORING THE DRILLING OF A WELLBORE

CROSS-REFERENCE TO RELATED APPLICATIONS

This application claims priority to and the benefit of European Patent Application No. 16290024.5, titled "Method and System for Monitoring The Drilling of A Wellbore," filed Feb. 4, 2016, the entire disclosure of which is hereby incorporated herein by reference.

BACKGROUND

The disclosure relates to a method and system for monitoring the drilling of a wellbore.

Usually a wellbore is drilled with a drilling bit, the cuttings generated during drilling being brought to the surface by a drilling fluid, generally mud that is injected in the wellbore and pushed back to the surface, carrying the cuttings.

When drilling a wellbore, several parameters are measured to monitor the drilling of the wellbore, some of them being related to the drilling fluid. However, none of the current measurements enable to determine accurately reliable drilling indicators relative to the drilling fluid, in particular concerning the recirculation of drilling fluid.

SUMMARY

The disclosure relates to a method and system for monitoring the drilling of a wellbore.

In particular, one aspect of the disclosure relates to a method of monitoring the drilling of a wellbore, wherein a drilling fluid circulates in the wellbore during drilling, the method comprising:
  Extracting a plurality of gaseous compound from a sample of drilling fluid exiting the wellbore,
  Measuring a quantity y(i) of a group of compounds comprising one or several extracted gaseous compound,
  Determining, from the measured quantity y(i) and an extraction coefficient ρ(i) associated to each group, the content x(i) of each group of gaseous compounds present in the sample of drilling fluid,
  Deriving (116) a drilling indicator from the content x(i) of at least one group of gaseous compounds, The method may comprise one or more of the features listed below:
  the extracted gaseous compounds comprise hydrocarbons, in particular alkanes,
  the drilling indicator is derived from the content x(i) of one or several groups of compounds consisting of hydrocarbons. It may be an indication of a mud cut,
  the method comprises measuring or determining at least one additional parameter relative to the wellbore and/or the drilling conditions. The additional parameters may comprise a temperature, a pressure, a torque or RPM (rotation per minute), an injection pump flow (IF), a rate of penetration (ROP), a borehole diameter or an hole size (HS), a drilling fluid density (D).
  the drilling indicator is derived according to the following formula:

$$N\ TG = 14.71 \frac{0.2642 \times IF}{3.281\ ROP\ (HS)^2}$$

wherein $x = \Sigma_1^n x(i)$, i being the index identifying each group of compound IF is the injection pump flow (l/min), HS is the Hole Size of the borehole (inches)

ROP is the rate of penetration of the drill bit in the formation (m/hr).

the method comprises taking a decision relative to drilling based on the drilling indicator and optionally one or several additional parameters, the decision comprises determining if the drilling fluid will be recirculated.

the decision may be taken based on the drilling indicator and a density of the drilling fluid, the method comprises determining the extraction coefficient ρ(i), determining the extraction coefficient may comprise calibrating an extraction device by performing successive extractions of at least a calibration compound of a calibration sample of drilling fluid and measuring the extracted quantity of the calibration compound at each successive extraction the method comprises preparing the calibration sample by adding at least one liquid alkane to a sample of drilling fluid, the extraction coefficient is determined based on at least one or several extraction coefficients associated to previous extractions. The extraction coefficient is determined by statistical processing of a plurality of extraction coefficients associated to previous extractions, the previous extractions being optionally chosen on the basis of at least one mud parameter and/or extraction condition.

the drilling fluid is heated before the extraction of the gas compound, the method comprises controlling the extraction conditions while extracting, the extraction conditions comprising at least one of a temperature of the drilling mud in the extraction device, a drilling fluid flow rate $Q_m$ admitted in an enclosure of the extraction device, an extracted gas flow rate $Q_g$, a volume $V_m$ of drilling fluid in the enclosure, a gas volume Vg present in the enclosure, a stirring rate of a stirring device for stirring the drilling fluid in the enclosure.

Another aspect of the disclosure also relates to a system for monitoring the drilling a wellbore, in which a drilling fluid circulates in the wellbore during drilling, the system comprising:
  An extraction device for extracting a plurality of gaseous compounds from a sample of the drilling fluid exiting the wellbore,
  A measuring device for measuring a quantity y(i) of at least a group of compounds of the plurality, wherein each group comprises at least one extracted gaseous compound,
  at least a processing unit) for:
    i. determining, from the measured quantity y(i) and a predetermined extraction coefficient ρ(i) associated to each group, the content x(i) of each group of gaseous compounds in the sample of drilling fluid,
    ii. Deriving a drilling indicator from the content x(i) of at least one group of gaseous compounds.

The method and system according to the disclosure enable to determine accurately at least one drilling indicator related to the drilling fluid and to take smart drilling decisions based on this indicator.

BRIEF DESCRIPTION OF THE DRAWINGS

Various aspects of this disclosure may be better understood upon reading the following detailed description and upon reference to the drawings in which.

DETAILED DESCRIPTION

One or more specific embodiments of the present disclosure will be described below. These described embodiments are examples of the presently disclosed techniques. Additionally, in an effort to provide a concise description of these embodiments, some features of an actual implementation may not be described in the specification. It should be appreciated that in the development of any such actual implementation, as in any engineering or design project, numerous implementation-specific decisions may be made to achieve the developers' specific goals, such as compliance with system-related and business-related constraints, which may vary from one implementation to another. Moreover, it should be appreciated that such a development effort might be complex and time consuming, but would still be a routine undertaking of design, fabrication, and manufacture for those of ordinary skill having the benefit of this disclosure.

When introducing elements of various embodiments of the present disclosure, the articles "a," "an," and "the" are intended to mean that there are one or more of the elements. The terms "comprising," "including," and "having" are intended to be inclusive and mean that there may be additional elements other than the listed elements. Additionally, it should be understood that references to "one embodiment" or "an embodiment" of the present disclosure are not intended to be interpreted as excluding the existence of additional embodiments that also incorporate the recited features. In all the following, the terms "upstream" and "downstream" are to be understood relatively to the normal direction of circulation of a fluid in a conduit.

Figure 1:
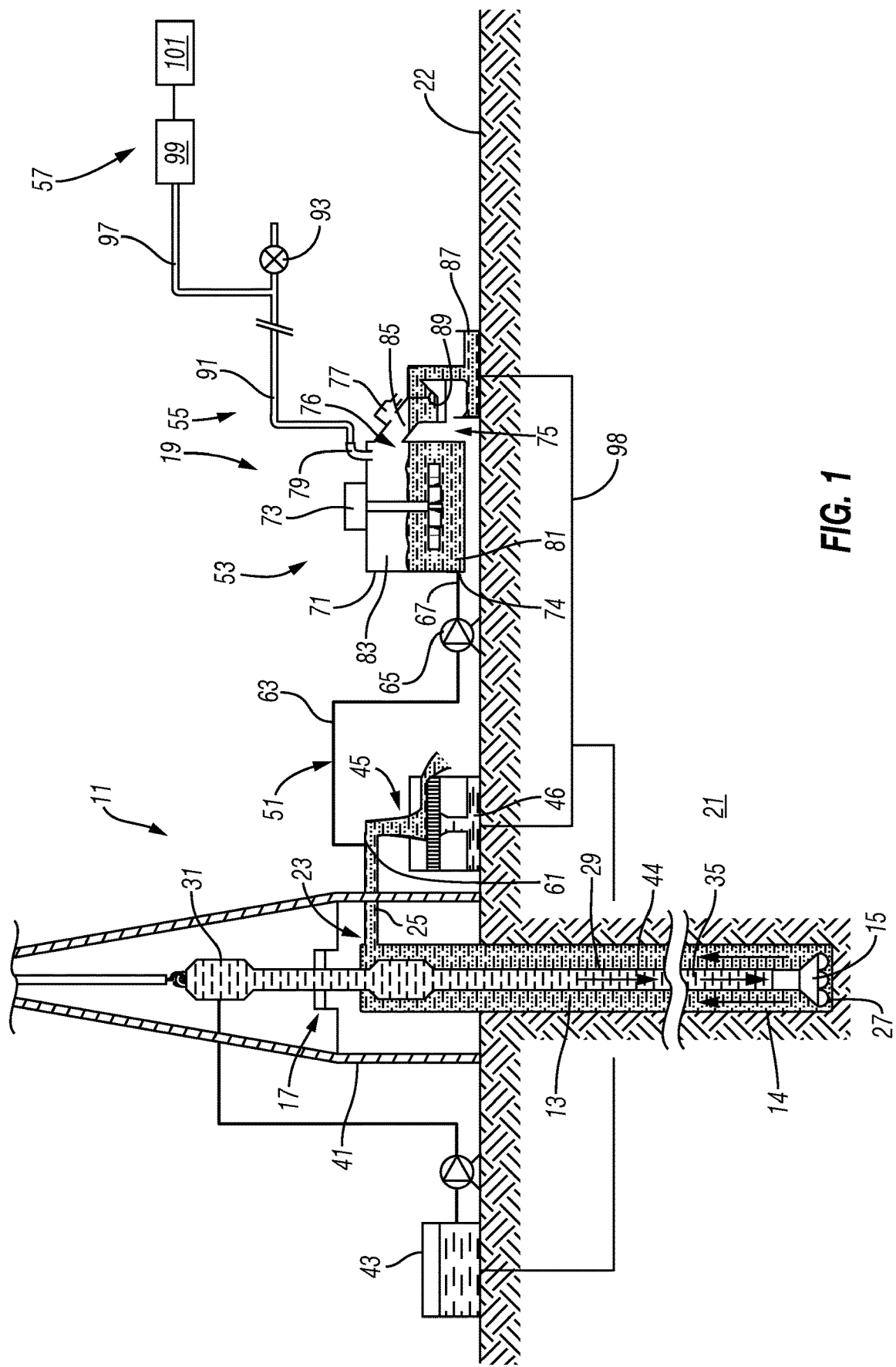
FIG. 1 is a schematic view of an embodiment of a system according to the disclosure.

With reference to FIG. 1, a drilling installation 11 is described. The drilling installation 11 comprises of a well for producing fluid, notably hydrocarbons, such as an oil well.

This installation 11 comprises a drilling conduit 13 positioned in a cavity 14 pierced by a rotary drilling tool 15 in a subsoil 21, a surface installation 17, and an assembly 19 for monitoring the drilling of a wellbore, in particular analyzing the gases contained in the drilling mud exiting the well.

The drilling conduit 13 includes at the surface 22 a well head 23 provided with a conduit 25 for circulation of the fluid in the wellbore.

The drilling tool 15 comprises, from bottom to top in FIG. 1, a drilling head 27, a drill string 29, and a head 31 for injecting drilling fluid. The drilling tool 15, is driven into rotation by the surface installation 17.

The drilling head 27 is mounted on the lower portion of the drill string 29 and is positioned in the bottom of the cavity 14.

The string 29 comprises a set of hollow drilling tubes. These tubes delimit an inner space 35 which allows the drilling fluid injected through the head 31 from the surface 22 to be brought as far as the drilling head 27.

This drilling fluid, commonly designated with the term of <<drilling mud>>, is essentially liquid.

The surface installation 17 comprises a system 41 for supporting and driving into rotation the drilling tool 15, a system 43 for injecting the drilling fluid and a vibrating sieve 45.

The injection system 43 is hydraulically connected to the injection head 31 for introducing and circulating the drilling fluid in the internal space 35 of the drill string 29.

The drilling fluid is introduced into the inner space 35 of the drill string 29 through the injection system 43. This fluid flows downwards down to the drilling head 27 and passes into the drilling conduit 13 through the drilling head 27. This fluid cools and lubricates a drilling head 33. The fluid collects the solid debris resulting from the drilling and flows upwards through the annular space defined between the drill string 29 and the walls of the drilling conduit 13, and is then discharged through the circulation conduit 25.

The inner space 35 opens out facing the drilling head 27 so that the drilling fluid lubricates the drilling head 33 and flows upwards in the cavity 14 along the conduit 13 up to the well head 23, while discharging the collected solid drilling debris, in the annular space 44 defined between the string 29 and the conduit 13.

The circulation conduit 25 is hydraulically connected to the cavity 14, through the well head 23 in order to collect the drilling fluid from the cavity 14. It is for example formed by an open mud conduit or by a closed tubular conduit.

The vibrating sieve 45 collects the fluid loaded with drilling residues which flow out of the circulation conduit 25, and separates the liquid from the solid drilling residues, storing the liquid in one or several tanks 46.

The monitoring assembly 19 comprises a device 51 for sampling drilling mud in the conduit 25, an extraction system for extracting gases contained in the drilling mud, a transport device 55 for transporting the extracted gases, a measuring device 57, and a computer 101 comprising one or more processing units and connected to the measuring device 57.

The sampling device 51 comprises a sampling head 61 immersed in the circulation conduit 25, a sampling conduit 63 connected upstream to the sampling head 61.

The extraction system comprises a pump 65 downstream of the sampling conduit 63, an extraction device 53 for performing a gas extraction and a mud discharge conduit 75.

The pump 65 is for example a peristaltic pump capable of conveying the drilling mud sampled by the head 61 towards the extraction device 53 with a determined mud volume flow rate Qm.

The extraction device comprises an enclosure 71, and a rotary stirrer 73 mounted in a projecting manner in the enclosure 71 and for instance rotatably driven by a motor mounted on the upper portion of the enclosure.

The extraction device may comprise a flow meter and a mud heater (not represented here) hydraulically connected in series between the pump 65 and the enclosure 71. The heater may enable to heat the mud at a predetermined temperature, in order to facilitate the extraction. When mud is heated a least part of the liquid compounds such as hydrocarbon contained in the mud may be transformed into gaseous compounds.

The enclosure 71 has a mud inlet 74 for receiving a flow of drilling mud from the sampling device 51, and a mud outlet 76 for releasing the mud from the enclosure into the discharge conduit 75.

The discharge conduit 75 comprises, in succession, an overflow passage 85, which is a downwardly inclined upstream portion, which forms an angle of approximately 45° with the horizontal, a siphonforming bent portion 89, and a substantially vertical downstream portion 87 which is open at its lower end, above the level of the liquid contained in the enclosure.

The drilling fluid introduced into the enclosure 71 via the supply conduit 67 is discharged by overflow into the discharge conduit 75 through the overflow passage 85. A portion of the discharged fluid temporarily lies in the siphon 89 which prevents gases from entering the upper portion 83 of the enclosure 71 through the discharge conduit 75. The mud collected in the discharge conduit 75, as well as the mud stored in tank 46, may be recycled to the injection system 43 by the way of a pipe 98 for recirculating mud.

The enclosure 71 also has a gas inlet 77 for injecting a carrier gas at a flow rate $Q_g$, and a gas outlet 79 for recovering the extracted gas.

The enclosure 71 has an inner volume for example comprised between 0.04 L and 3 L. It defines a lower portion 81 containing the drilling fluid stemming from the supply conduit 67 and an upper portion 83 defining a gas head space above the drilling fluid. The volume of mud $V_m$ may be kept constant by controlling the flow of drilling fluid $Q_m$ and the volume of the upper portion $V_g$, corresponding to the volume of the enclosure minus the volume of the mud $V_m$ is therefore kept constant as well. The mud outlet 76 opens out into the lower portion 81.

The gas outlet 79 is connected to the transport device 55.

The stirrer 73 is immersed into the drilling mud present in the lower portion 81. It is capable of vigorously stirring the drilling mud in order to extract at least a drilling compound to be analyzed or a calibration compound present in the drilling mud.

In the example shown, the carrier gas is formed by the surrounding air around the installation, at atmospheric pressure. Alternatively, this carrier gas is another gas such as nitrogen or helium.

The temperature of the drilling mud, the pressure P of the gas head space located above the mud in the upper portion 83 of the enclosure 72, the drilling mud flow rate Qm admitted in the enclosures, and the extracted gas flow rate Qg, the volume Vm of drilling mud in the enclosure, the gas volume Vg present in the enclosures, the nature of the stirring as well as the stirring rate, may be controlled so that the extraction conditions remain substantially constant.

The transport device 55 comprises a line 91 for transporting the extracted gas or the towards the measuring device 57, and a suction system 93 for conveying the extracted gases through the transport line 91. The line 91 can be manufactured from a polymeric material, especially polyethylene, and has, for example, a length ranging from 5 meters to 500 meters if the measuring device 57 is situated in a cabin, remote from the wellsite and outside of an explosive region of the wellsite, or from 0 to 5 meters when the measuring device 57 is situated at the wellsite, in the explosive region.

The measuring device 57 comprises a sampling conduit 97 tapped on the transport line 91 upstream from the suction system 93, and an instrumentation 99.

The instrumentation 99 is capable of detecting and quantifying at least a compound in the extracted gas transported through the transport line 91.

This instrumentation 99 for example comprises infrared detection apparatuses, chromatographs with flame ionization detectors (FID) and/or thermal conductivity detectors (TCD) depending on the gases to be analyzed.

It may also comprise a chromatography system coupled with a mass spectrometer, this system being designated by the acronym "GC-MS". It may comprise an isotope analysis apparatus as described in Application EP-A-1 887 343 of the Applicant. The instrumentation may comprise one or more measuring devices.

Online simultaneous detection and quantification of a plurality of drilling compounds contained in the fluid, without any manual sampling by an operator, is therefore possible within time intervals of less than 1 minute.

The drilling fluid for example is formed by oil-based mud (having oil as a main component) or water-based mud (having water as a main component). In general, drilling mud compounds contain at least hydrocarbons with $C_a$ with n<20. The hydrocarbon compounds that are analyzed are usually up to $C_8$, however higher $C_n$ ones can be analyzed if needed.

The computer 101 comprises one or several processing units. It is connected by a network to the instrumentation 99. It may comprise also at least a memory, for storing for instance a database and may be in communication with one or several other computers locally or remotely, via one or several networks.

The monitoring assembly 19 may also comprise one or more additional sensors (not shown on the drawings) to provide measurements relative to the drilling. From this measurement, drilling parameters may be derived. These drilling parameters may be directly measured by the sensors or determined from the measurements of one or several additional sensors, for instance by the computer 101. The sensors may measure parameters relative to the drilling fluid, to the drilling installation or to the wellbore, and may be located anywhere at the well site, for instance at the surface or downhole.

A method 100 according to the disclosure will now be disclosed.

The method comprises recovering (block 102) drilling fluid exiting the wellbore, sampling (block 104) the drilling fluid via the sampling device 51, extracting (block 106) gases from the drilling fluid via the extraction device 53 and measuring (block 108) with the measuring device 57 a quantity y(i) of one or a plurality of gas compounds extracted from the drilling mud, as it has been described earlier. An index i is used to identify the gas compounds.

The method also comprises determining a content x(i) of the or the plurality of the gas compounds present in the drilling fluid from the measured quantity y(i).

Determining the content x(i) of gas compounds in the drilling fluid according to the disclosure may be performed as follows.

It comprises first obtaining (block 111) an extraction coefficient ρ(i) relative to a first compound or a first group of compounds and then correcting (block 110) the measured quantity y(i) relative to the first compound or a first group of compounds with the extraction coefficient ρ(i) in order to obtain the actual content x(i) of said compound or group of compounds in the drilling mud.

Figure 2:
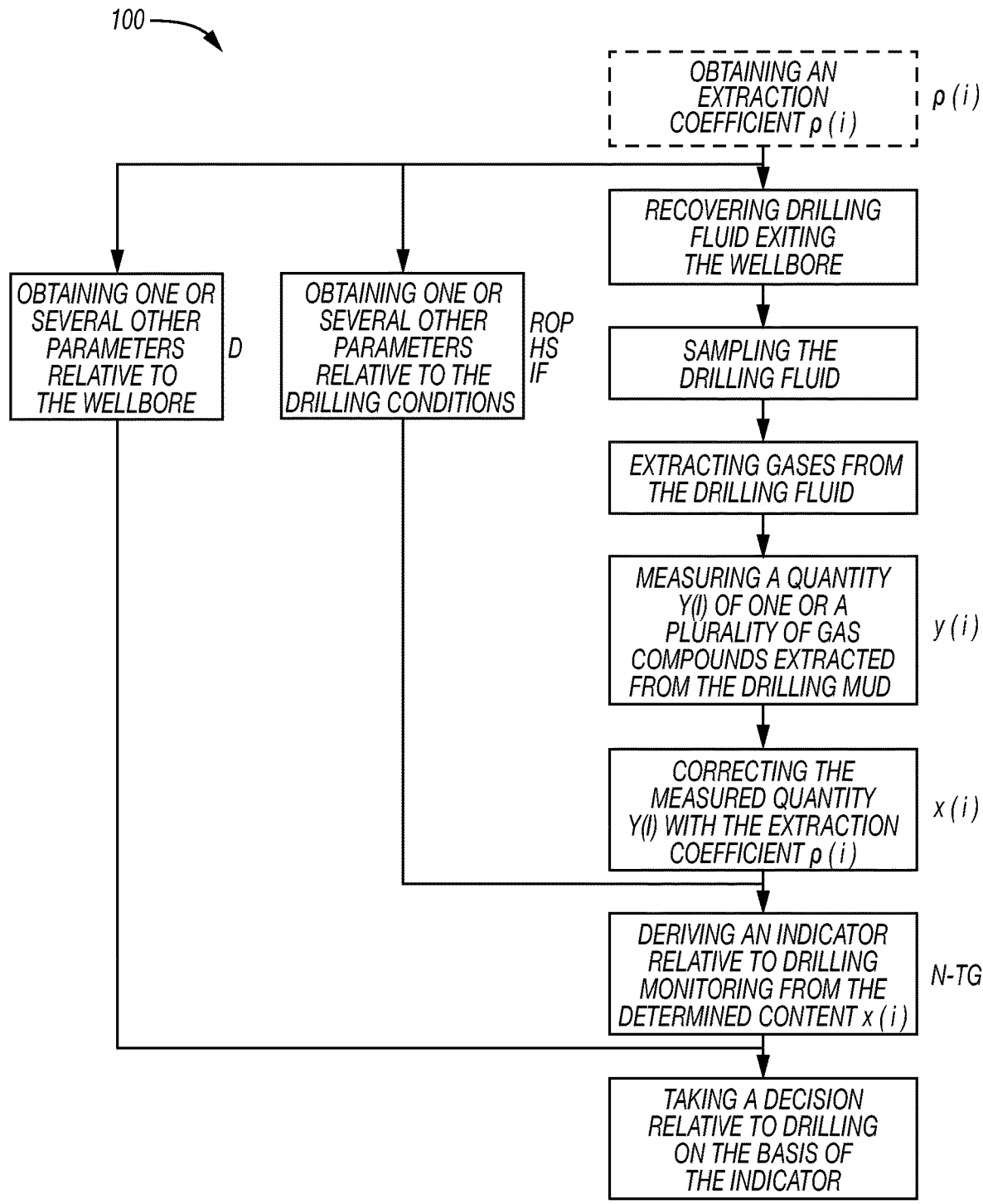
FIG. 2 is a flowchart of a method according to an embodiment of the disclosure.

Obtaining the extraction coefficient ρ(i) may comprise, in the embodiment of FIG. 2, calibrating the extraction device before extracting the gas from the drilling fluid. Calibration may for instance comprise successively submitting a predetermined sample of drilling fluid to several extraction stages in the extraction device 53, the amount of extracted gas being measured at each extraction stage. This method is known as "multi-pass" calibration method and is described in more details in application EP-A-1 710 575 filed by the Applicant.

When the extraction conditions of the first extraction and the $n^{th}$ extraction with the extraction device are similar, the parameters relative to a predetermined compound or group of compounds i may be linked by the following equation:

$$y_n(i) = y_1(i) \times \exp[-m(i) \times (n-1)] \quad (1)$$

wherein $y_j$ is the quantity of extracted gas measured at the $j$th extraction m(i) is a coefficient relative to the compound or group of compound i The extraction coefficients ρ(i) for the compound or group of compound is for example calculated by the computer 101 with the following formula:

$$\rho(i) = \frac{1}{y_1(i)} \sum_1^\infty y_n(i) = \frac{1}{1 - \exp(-m(i))} = \frac{1}{1 - \lambda(i)}, \quad (2)$$

wherein $\lambda(i) = y_1(i)/y_2(i)$

As explained in EP-A-2 380 017, the calibration may be performed using a first group of hydrocarbon compounds and extrapolating the results to a second group of compounds.

The calibration may be performed with a drilling fluid coming from the wellbore or with a synthetic sample of drilling fluid prepared by injecting liquid alkanes into a drilling mud sample for performing calibration before the beginning of the drilling phase, as disclosed in US-A-2014/067307.

The calibration may be also performed in any other suitable way, for instance by extracting progressively the gas from an enclosure in which a sample of drilling fluid remains stagnant and does not flow, as described in EP patent application 15290313.4 not published yet. This does not necessitate several passages of the sample in the extraction device 53.

Alternatively, determining the extraction coefficient may also be performed without calibrating the extraction device, for instance in view of statistical handling of extraction coefficients obtained from previous extractions performed in another location (wellsite or lab) and/or with another extraction device, potentially taking into account the coefficients obtained from previous extractions in which the mud parameters and/or extraction conditions are the same as for the current extraction. Such a method is for instance described in EP patent application 15290274.8, not published yet. A database comprising extraction coefficients, optionally associated with drilling conditions and/or mud parameters, may be stored on the computer 101 and/or any other computer to which the computer is connected. The extraction coefficients ρ(i) that will be used relative to the current extraction may also be determined in advance, the result only being stored on the computer 101.

An extraction coefficient ρ(i) may be for instance determined for each compound as disclosed in EP-A-1 710 575 but a unique extraction coefficient may also be determined for a group comprising several compounds.

Once the extraction coefficient is obtained, the correction (block 110) is performed for each compound or group of compound for instance using the following equation:

$$x(i) = \frac{Q_g}{Q_m} \cdot \rho(i) \cdot y(i). \quad (3)$$

The method may also comprise obtaining (blocks 112 and 114) one or several other parameters relative to the drilling conditions and/or the wellbore. These parameters may be directly measured, downhole or at the surface, with appropriate sensors, and/or determined thanks to one or several measurements. These parameters may comprise one or several of the following:

A temperature,
A pressure,
A torque or RPM (rotation per minute),
An injection pump flow (IF),
A rate of penetration (ROP),
A borehole diameter or hole size (HS),
A drilling fluid density (D) that may be measured at injection of the mud in the wellbore and/or at the exit of the mud from the wellbore.

The method then comprises (block 116) deriving an indicator relative to drilling monitoring from the determined content x(i).

The indicator may be the following:

$$N\ TG = 14.71 \frac{0.2642 \times IF}{3.281\ ROP\ (HS)^2} \quad (4)$$

wherein $x = \Sigma_1^n x(i)$.
wherein IF is expressed in l/mn, ROP is expression in m/hr and HS is expressed in inches.

Other drilling indicators may also be derived to monitor the drilling. The drilling indicator gives an indication of the mud cut.

The method then comprises (block 118) taking a decision relative to drilling on the basis of the indicator. This decision may be more particularly related to the recirculation of drilling fluid, ie will enable to determine whether the drilling fluid exiting the wellbore should be reinjected in the wellbore or not. The decision relative to the drilling may be taken on the basis of the indicator alone or in combination with one or several other parameters relative to the wellbore and/or the drilling conditions, such as a density of the drilling fluid.

The system and method according to the disclosure enable to provide accurate indicators that help taking smart decisions relative to drilling, and in particular relative to the use of the drilling fluid.

In view of the entirety of the present disclosure, including the figures, a person skilled in the art should appreciate that they may readily use the present disclosure as a basis for designing or modifying other processes and structures for carrying out the same uses and/or achieving the same aspects introduced herein. A person skilled in the art should also realize that such equivalent constructions do not depart from the spirit and scope of the present disclosure, and that they may make various changes, substitutions and alterations herein without departing from the spirit and scope of the present disclosure. For example, although the preceding description has been described herein with reference to particular means, materials and embodiments, it is not intended to be limited to the particulars disclosed herein; rather, it extends to functionally equivalent structures, methods, and uses, such as are within the scope of the appended claims.

The invention claimed is:

1. A method of monitoring the drilling of a wellbore, wherein a drilling fluid circulates in the wellbore during drilling, the method comprising:

Extracting a plurality of gaseous compounds from a sample of drilling fluid exiting the wellbore, Measuring a quantity y(i) of at least a group of compounds, wherein each group comprises at least one extracted gaseous compound, Determining, from the measured quantity y(i) and an extraction coefficient ρ(i) associated to each group, the content x(i) of each group of gaseous compounds present in the sample of drilling fluid, Deriving a drilling indicator from the content x(i) of at least one group of gaseous compounds, wherein the drilling indicator is an indication of a mud cut.

2. The method according to claim 1, wherein the extracted gaseous compounds comprise hydrocarbons and wherein the drilling indicator is derived from the content x(i) of one or several groups of compounds consisting of hydrocarbons.

3. The method according to claim 2, wherein the extracted gaseous compounds comprise alkanes.

4. The method according to claim 1, comprising measuring or determining at least one additional parameter relative to the wellbore and/or the drilling conditions.

5. The method according to claim 4, wherein the at least one additional parameters comprise at least one parameter of the following list:

A temperature,
A pressure,
A torque or RPM (rotation per minute),
An injection pump flow (IF),
A rate of penetration (ROP),
A borehole diameter or hole size (HS),
A drilling fluid density (D).

6. The method according to claim 5, wherein the drilling indicator is derived according to the following formula:

$$N - TG = 14.71 \frac{0.2642 \cdot x \cdot IF}{3.281 \cdot ROP \cdot (HS)^2}$$

wherein $x = \Sigma_1^n x(i)$, i being the index identifying each group of compound IF is the injection pump flow (1/min),
HS is the Hole Size of the borehole (inches)
ROP is the rate of penetration of the drill bit in the formation (m/hr).

7. The method according to claim 1, comprising taking a decision relative to drilling based on the drilling indicator.

8. The method according to claim 7, wherein the decision comprises determining if the drilling fluid will be recirculated.

9. The method according to claim 8, wherein decision is taken based on the drilling indicator and the density of the drilling fluid.

10. The method according to claim 9, comprising determining the extraction coefficient ρ(i).

11. The method according to claim 10, wherein determining the extraction coefficient comprises calibrating an extraction device by performing successive extractions of at least a calibration compound from a calibration sample of mud and measuring the extracted quantity of the calibration compound at each successive extraction.

12. The method according to claim 11, comprising preparing the calibration sample by adding at least one liquid alkane to a sample of drilling fluid.

13. The method according to claim 7, wherein the decision is also taken based on one or several parameters.

14. The method according to claim 1 wherein the extraction coefficient is determined based on at least one or several extraction coefficients associated to previous extractions.

15. The method according to claim 14, wherein the extraction coefficient is determined by statistical processing of a plurality of extraction coefficients associated to previous extractions.

16. The method according to claim 15, wherein the previous extractions are chosen on the basis of at least one mud parameter and/or extraction condition.

17. The method according to claim 1, wherein the drilling fluid is heated before the extraction of the gas compound.

18. The method according to claim 1, comprising controlling the extraction conditions while extracting, the extraction conditions comprising at least one of the parameters of the following list:

a temperature of the drilling mud in the extraction device,
a drilling fluid flow rate $Q_m$ admitted in an enclosure of the extraction device,
an extracted gas flow rate $Q_g$,
a volume $V_m$ of drilling fluid in the enclosure,
a gas volume $V_g$ present in the enclosure,
a stirring rate of a stirring device for stirring the drilling fluid in the enclosure.

19. A system for monitoring the drilling a wellbore, wherein a drilling fluid circulates in the wellbore during drilling, the system comprising an extraction device for extracting a plurality of gaseous compounds from a sample of the drilling fluid exiting the wellbore, and a measuring device for measuring a quantity y(i) of at least a group of compounds of the plurality, wherein each group comprises at least one extracted gaseous compound, at least a processing unit for:

i. determining, from the measured quantity y(i) and a predetermined extraction coefficient ρ(i) associated to each group, the content x(i) of each group of gaseous compounds present in the sample of drilling fluid, ii. Deriving a drilling indicator from the content x(i) of at least one group of gaseous compounds, wherein the drilling indicator is an indication of a mud cut.

* * * * *